US 6,998,421 B2

(12) United States Patent
Keller

(10) Patent No.: US 6,998,421 B2
(45) Date of Patent: Feb. 14, 2006

(54) COMPOUNDS AND METHODS FOR INHIBITION OF PHOSPHOLIPASE $A_2$ AND CYCLOOXYGENASE - 2

(75) Inventor: Brian Keller, Pittsburg, CA (US)

(73) Assignee: Biozone Laboratories, Inc., Pittsburg, CA (US)

( * ) Notice: Subject to any disclaimer, the term of this patent is extended or adjusted under 35 U.S.C. 154(b) by 264 days.

(21) Appl. No.: 10/229,195

(22) Filed: Aug. 26, 2002

(65) Prior Publication Data

US 2003/0109580 A1   Jun. 12, 2003

Related U.S. Application Data

(63) Continuation of application No. 09/877,334, filed on Jun. 7, 2001, now Pat. No. 6,495,596.

(51) Int. Cl.
   *A01N 37/10* (2006.01)
(52) U.S. Cl. .............. 514/533; 514/886; 514/825; 514/944; 514/962; 554/115; 554/121; 554/224
(58) Field of Classification Search ........... 514/533, 514/884, 825, 944, 963; 584/118, 121, 224
See application file for complete search history.

(56) References Cited

U.S. PATENT DOCUMENTS

| | | | |
|---|---|---|---|
| 5,001,234 A | 3/1991 | Bundy et al. |
| 5,122,536 A | 6/1992 | Perricone |
| 5,318,970 A | 6/1994 | Suzuki et al. |
| 5,451,686 A | 9/1995 | Garst |
| 5,659,049 A | 8/1997 | Franson et al. |
| 5,905,088 A | 5/1999 | Diaz et al. |
| 6,060,082 A | 5/2000 | Chen et al. |
| 6,060,085 A | 5/2000 | Osborne |
| 6,143,770 A | 11/2000 | Lane et al. |

FOREIGN PATENT DOCUMENTS

EP   19909552 A1   7/2000

*Primary Examiner*—Deborah D. Carr
(74) *Attorney, Agent, or Firm*—Gregory Scott Smith; GSS Law Group

(57) ABSTRACT

The present invention comprises a group of related lipid molecules, and methods for their use, that maybe used to treat inflammation and certain inflammation related diseases. The group of related lipid molecules are capable of inhibiting certain enzyme systems including phospholipase $A_2$, and cyclooxygenase-2. The group of related lipid molecules of the invention may be characterized by specific structural characteristics, or by specific biological activity, including inhibition of the previously listed enzymes.

60 Claims, 5 Drawing Sheets

COMPOUNDS AND METHODS FOR INHIBITION OF PHOSPHOLIPASE A₂ AND CYCLOOXYGENASE - 2

CROSS REFERENCE TO RELATED APPLICATION

This application is a Continuation of, and claims the priority date of, patent application Ser. No. 09/877,334 filed Jun. 7, 2001 now U.S. Pat. No. 6,495,596, entitled: Compounds for Inhibition of Phospholipase A2 and Cyclooxygenase-2.

FIELD OF THE INVENTION

The present invention relates to a group of compounds and a method for inhibiting certain enzyme systems that mediate a variety of physiological responses in mammals. More particularly, the present invention relates to a compound and method for inhibition of phospholipase $A_2$, and cyclooxygenase-2, which are enzymes that catalyze a cascade of biochemical reactions that lead to the mediation of pain, fever, inflammation and other functions.

BACKGROUND OF THE INVENTION

Human beings and other mammals spend energy continuously defending against a vast array of invasive pathogenic organisms including bacteria, viruses, fungi and other intracellular and extra-cellular parasites in addition to other potentially harmful agents that are capable of upsetting homeostasis. In response, humans and other mammals maintain many mechanisms capable of processing and defending against such antigens and agents. The biological response to attack and injury is mediated through the formation of a series of structurally related compounds called eicosanoids, which include the prostaglandins, the leukotrienes, and the thromboxanes. Master enzymes known as phospholipase $A_2$ and phospholipase C regulate the formation of these highly potent compounds.

Phospholipase $A_2$ is a heat-stable, calcium dependent enzyme that catalyses the hydrolysis of the 2-acyl bond of 3-n-phosphoglycerides. It has a molecular weight of about 30,000 Daltons. Phospholipase $A_2$ has been found in many human tissues including platelets, chondrocytes, placenta, cartilage, peritoneal calls and peritoneal fluid and spleen. (Vades, p., Puzanski, W., *Soluble phospholipase A₂ in human pathology: clinical-laboratory interface.* Biochemistry, molecular biology, and physiology of phospholipase $A_2$ and its regulatory factors. Ed A B Mukherjee, Plenum Press, New York, 1990.) High levels of phospholipase $A_2$ are found in synovial tissue and it has been shown that activity of rheumatoid arthritis significantly correlated to the levels of serum phospholipase $A_2$. (Vadas, P., Pruzanski, W. and Stefanski, E., *Characterization of extracellular phospholipase A2 in human synovial fluids.* Life Sci. 36: 579, 1985.)

Substantial evidence has been found (above reference) that excessive concentrations of extra-cellular phospholipase $A_2$ may initiate and propagate inflammation and cause cellular damage. In addition phospholipase $A_2$ was also found to modulate various aspects of phagocytic activity, vascular tone and permeability. A strong correlation between phospholipase $A_2$ activity and certain human diseases have also been identified. A few such diseases are listed in table 1 below.

| DISEASE | LOCATION OF PHOSPHOLIPASE $A_2$ |
| --- | --- |
| Rheumatoid arthritis | Serum, synovial fluid |
| Osteoarthritis | Synovial fluid |
| Psoriasis | Synovial fluid |
| Monoarthritis | Synovial fluid |
| Gout | Synovial fluid |
| Collagen Vascular Disease | Serum |
| Pancreatitis | Serum |
| Peritonitis | Peritoneal fluid |
| Sepsis and Shock | Serum |
| Renal Failure | Serum |

FIG. 1 illustrates the key role that phospholipase $A_2$ and cyclooxygenase-2 are currently understood to play in the formation of potent, biologically active substances that mediate a variety of conditions and disease states. The process of the formation of prostaglandin's, leukotrienes, lipoxins, and thromboxanes in addition to lysosomal enzyme release, bactericidal activity, pro-inflammatory eicosanoids, PAF and lysophosphatides and reactive oxygen species, begins on the surface of specialized cells including osteoblasts, endothelial cells, chondrocytes, synoviocytes, and renal mesangial cells. The major constituents of these, and all other, cell membranes are phospholipids. The biochemical conversion of these important molecules to arachidonic acid is catalyzed by phospholipase $A_2$. Arachidonic acid is further converted to leukotrienes, lipoxins, thromboxanes and prostaglandins. The latter two species are formed by way of chemical conversion catalyzed by two other important enzymes known as cyclo-oxygnease-1 and cyclooxygenase-2. The arachidonic acid cascade is a well know pathway leading to the mediation of pyrogenicity, vasoconstriction, increased vascular permeability, contraction of smooth muscle, inflammation, and pain.

Found in every cell of the human body, albeit to varying degrees, prostaglandins have profound physiologic effects including mediation of pain and inflammation. The prostaglandins (PG) are a family of lipid-soluble hormone-like molecules produced by different cell types in the body. For example, macrophages and monocytes are large producers of both PGE2 and PGF2, neutrophils produce moderate amounts of PGE2, and masts cells produce PGD2. It is important to note that, unlike histamine, prostaglandins do not exist free in tissues vacuoles, but have to be synthesized and released in response to an appropriate stimulus. This synthesis is dependent on phospholipase $A_2$ and cyclooxygenase-2.

Thromboxanes are produced by monocytes and macrophages, as well as by platelets. Thromboxanes are involved in causing platelets to aggregate and constrict blood vessels and airways. These effects are some what opposed by the action of prostacyclin (PGI2), which is a potent vasodilator.

Leukotrienes (LT) exist in a number of varieties, and cause the chemotaxis (directed locomotion) and/or chemokinesis (general cell movement) of a number of cell types including neutrophils. The synthesis of LTB4 is inhibited by colchicines, an anti-flammatory agent used for treatment of gout. The mixture of LTC4, LTD4 and LTE4 originally called slow reacting substance of anaphylaxis is produced by a wide variety of smooth muscle, mainly in the bronchus, and have effects on mucous secretions. Inhibition of the formation of these substances is a useful therapeutic modality in asthma.

Lipoxins (LX) are a family of molecules that are thought to stimulate changes in microcirculation. For example, LXA4 induces rapid arteriolar dilation and can also antagonize LTD4-induced vasoconstriction. This suggests that LXA4 may regulate the action of vasoconstrictor leukotrienes. LXA4 can block neutrophil chemotaxis induced both LTB4 and N-formyl-oligopeptieds. Both LXA4 and LXB4 inhibit cytoxicity of natural killer T cells and thus there inhibition can be useful in allowing the immune system to remain intact while fighting infections and cancer.

Inflammation is a complex response of the body in response to damage of its cells and vascular tissues. The elucidation of the detailed processes of inflammation has revealed a close relationship between inflammation and the immune response. Basic symptoms of inflammation include redness, swelling, heat, pain, and deranged function. These signs and symptoms are thought to be due to extravasation of plasma and infiltration of leukocytes into the site of inflammation, as a result of cell damage. Early investigators considered inflammation a primary host defense system. Indeed inflammation is the key reaction of the immune response, but in fact, inflammation is more than this, since it can lead to death, as anaphylactic shock, or debilitating diseases, as in arthritis or gout.

What is needed is a novel lipid compound that is capable of reducing inflammation and certain related disease conditions, while avoiding disadvantages of the prior art, preferably without unacceptable side effects.

SUMMARY OF THE INVENTION

The present invention comprises a group of related lipid molecules, and methods for using the group of related lipid molecules, for inhibiting certain enzyme systems including phospholipase $A_2$ and cyclooxygenase-2, for the mediation of pain, fever, inflammation and other functions including phospholipase $A_2$ and cyclooxygenase-2. The ability of the group of related lipids of the invention to inhibit enzyme systems including phospholipase $A_2$ and cyclooxygenase-2 was surprising and unexpected. The group of related lipid molecules of the invention may be characterized by specific structural characteristics, or by specific biological activity, including inhibition of the previously listed enzymes. The group of related lipid molecules of the invention may be synthesized using known chemical methodologies, or isolated and purified from biological materials using known methods for isolating desired lipids. The group of related lipid molecules of the invention may be altered by known chemical means to produce various derivatives or analogues. This invention also relates to forms of the lipids of the invention which, upon administration to a patient, undergo biotransformation into an active form.

With regard to the structural characteristics, the group of related lipid molecules of the invention share and may preferably be characterized by the following three structural features: a backbone or linking structure, a polyethyleneglycol (PEG) chain, and a tail group having two long chain fatty acids. The long chain fatty acids preferably range between 11 and 25 (inclusive) carbons in length, and may be saturated, unsaturated, or polyunsaturated. Each long chain fatty acid is preferably of the same length, and saturation, but in some embodiments the chains may differ. The PEG groups may be various lengths, but is preferably between 100 and 5,000 daltons, and more preferably between 500 and 2,000 daltons. While a glycerol backbone or linking structure is preferred, in alternate embodiments, backbone structures including only two carbon, or more than three carbons may be useable. Furthermore, related compounds only a single long chain fatty acid or three long chain fatty acid s, instead of two long chain fatty acids, may also be effective in inhibiting phospholipase $A_2$ and cyclooxygenase-2, and are considered part of the current invention.

In a preferred embodiment, the lipid molecules of the invention, and compounds and mixtures thereof, may be administered to an animal or a humans as a pharmaceutical composition, a foodstuff, a food additive, a dietary supplement, or a cosmetic. The composition of the invention may be administered selectively or systemically, and delivery methods include but are not limited to oral and topical. The compound of the invention may be particularly suited for delivery as a component of a liposome or micelle. Useable systemic delivery methods may include but are not limited to use of the compound of the invention in the form of a tablet, a capsule, a syrup, a dragee, a suspension, an elixer, a solution, a powder, granules, an emulsion, microspheres, nanospheres, lipid vesicles, polymeric vesicles, or an injectable. Useable topical delivery methods may include but are not limited to use of the compound of the invention in the form of an ointment, a cream, a milk, an impregnated pad, a gel, a spray, and a lotion.

The invention also includes methods for administering the lipids of the invention in effective amounts through a variety of know means including as a pharmaceutical, foodstuff, dietary supplement, or cosmetic. Inflammation related diseases that may be treated include but are not limited to rheumatoid arthritis, osteoarthritis, psoriasis, monoarthritis, gout, collagen vascular disease, pancreatitis, peritonitis, sepsis and shock, renal failure.

DESCRIPTION OF THE PREFERRED EMBODIMENTS

The present invention comprises a novel group of related lipid molecules, and methods for using these molecules. The group of related lipid molecules of the invention (hereafter the "lipids of the invention") have the surprising and unexpected characteristic of inhibiting certain enzyme systems including phospholipase $A_2$ and cyclooxygenase-2, and are useful for reducing pain, fever, inflammation, inflammation related diseases, and other inflammation related functions.

In general, the group of related lipid molecules of the invention comprise a backbone, a polyethyleneglycol chain (hereafter "PEG chain"), and a tail group having preferably two hydrocarbon chains. Together, the PEG chain and the backbone comprise the head group of the molecule. The lipids of the invention may be synthesized using known chemical methodologies, or possibly isolated and purified from biological materials using known methods for isolating desired lipids, although natural occurrence of the lipids of the invention are not currently known to the inventors. The current preferred method of manufacturing the compounds of the invention include the well known steps of esterification of glycerine and carboxylic acid, followed by alkoxylation with ethylene oxide. The essential components in the preferred method of manufacture include selected carboxylic acid, glycerin and ethylene oxide molecules.

The lipids of the invention may be altered by known chemical means to produce various derivatives or analogues. Such derivative or analogue lipids may possess desired characteristics not possessed by the example lipids discussed herein, and such derivative or analogue lipids are considered to be included in this invention. Some of the group of related lipids of the invention, or their analogues, may be capable of undergoing biotransformation from a biologically inactive form into an active form upon administration to a patient.

Figure 1:
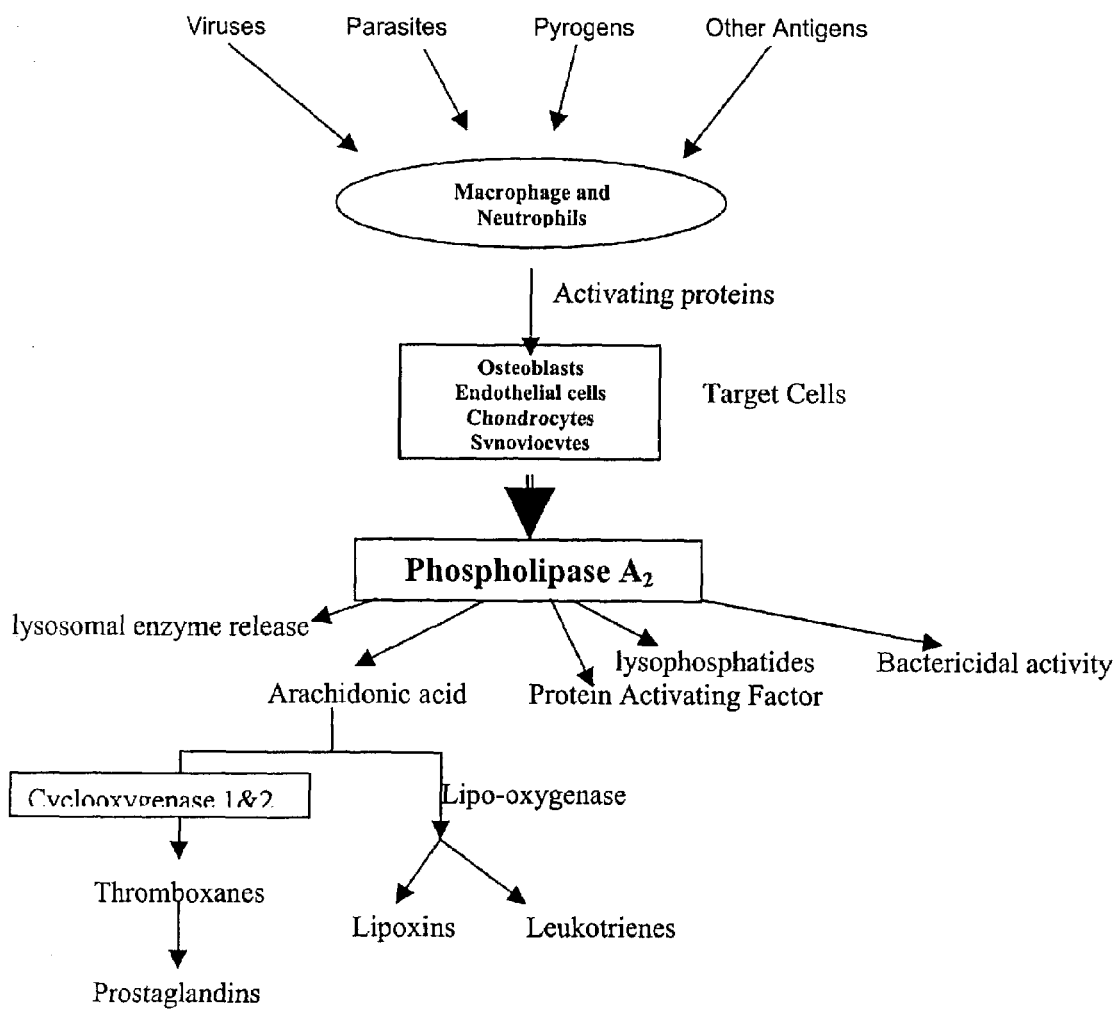
FIG. 1 illustrates the key role phospholipase $A_2$ and cyclo-oxygenase 1 and 2 are thought to play in the formation of, biologically active substances that mediate a variety of inflammation related conditions and disease states.
Figure 2:
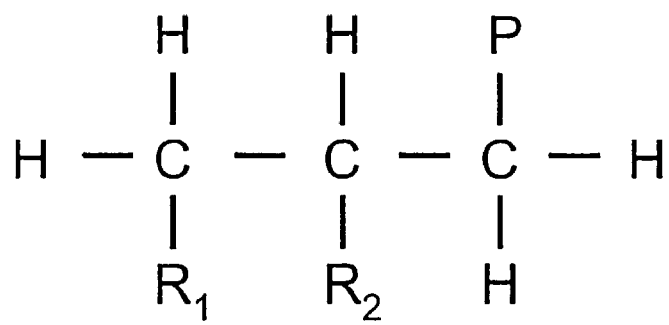
FIG. 2 illustrates a generic structural configuration of the group of lipid molecules of the invention

The group of related lipid molecules of the invention may be characterized by specific structural characteristics, and by the ability of the lipids of the invention to inhibit the activity of phospholipase $A_2$ and cyclooxygenase-2. With regard to the structural characteristics, the lipids of the invention share and may be characterized by the following structural features (as seen in FIG. 2):

(a) A head group P including a PEG chain. The size of the head group may be altered by varying the size of the PEG chain. The size of the PEG chain is preferably between 100 daltons and 5,000 daltons, and more preferably between 500 and 2000 daltons.

(b) A glycerol backbone. While a glycerol backbone or linking structure is preferred, in alternate embodiments, backbone structures including only two carbons, or more than three carbons may be useable.

(c) A tail group comprising $R_1$ and $R_2$, preferably comprising two long chain fatty acids preferably between 12 and 24 carbons in length, and preferably of equal size. The long chain fatty acids are preferably saturated, but may include cis double bonds between one or more carbon atoms. Both $R_1$ and $R_2$ are preferably of the same length, and saturation, but in some embodiments $R_1$ and $R_2$ may differ. In alternate embodiments, useable compounds may include only a single long chain fatty acid, or possibly three or more long chain fatty acids, if a backbone molecule longer than glycerol is used.

Figure 3:
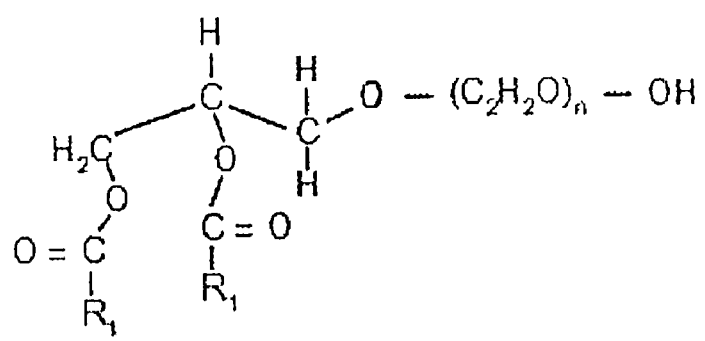
FIG. 3 illustrates another structural configuration of a lipid molecule of the group of related lipids of the invention.

In addition to the above-mentioned structural characteristics, the lipids of the invention may be characterized by biological activity. As will be discussed in more detail below, tests have been run to confirm the activity of the lipids of the invention with regard to the ability of the lipids of the invention to inhibit the activity of phospholipase A2. The lipids of the invention have also been found to inhibit the activity of cyclooxygenase-2, and possibly cyclo-oxygenase-1. Furthermore, the lipids of the invention have been proven through experimentation to be effective in reducing inflammation, and may be effective in the treatment of diseases or conditions including but not limed to: monoarthritis, gout, collagen vascular disease, pancreatitis, peritonitis, sepsis and shock, and renal failure. Some of the lipids of the invention may be further characterized by having a melting temperature, which allows a composition comprising the lipids to be in a liquid form when mixed with an aqueous solution. Generally this means that the lipid composition should have a phase transition temperature of between 0 degrees C. and 100 degrees C. The ability to be in a liquid form when mixed with an aqueous solution is preferable, but is not a necessary characteristic of the preferred embodiments of the group of related lipids of the invention. The formula below, also seen in FIG. 3, illustrates another generic structural configuration of a subset of the group of related lipid molecules of the invention:

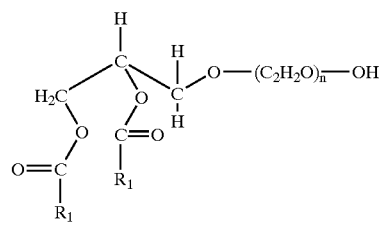

As before, $R_1$ and $R_2$ are preferably a long chain fatty acids between 12 and 24 carbons in length. The variable "n" is preferably an integer between 11 and 46. A number of specific derivatives of the a generic structural configuration of a subset of the group of related lipid molecules of the invention seen in FIG. 2 have been synthesized and tested for their ability to inhibit phospholipase A2 and cyclooxygenase-2. Table 2 below lists and describes a number of such derivatives.

| INCI Name of Lipid | Melting Point (Co) | Abbreviation | Structure |
|---|---|---|---|
| PEG-23 Glyceryl Dilaurate | Fluid @ 25° C. | PEG-23 GDL | $R_1, R_2 = CH_3(CH_2)_{10}$<br>n = 23 |
| PEG-12 Glyceryl Dioleate | Fluid @ 25° C. | PEG-12 GDO | $R_1, R_2 = H_3C(CH_2)_7\overset{\displaystyle H\quad H}{\underset{\displaystyle\diagup\quad\diagdown}{C=C}}(CH_2)_7$<br>n = 12 |

-continued

| INCI Name of Lipid | Melting Point (Co) | Abbreviation | Structure |
|---|---|---|---|
| PEG-23 Glyceryl Dioleate | Fluid @ 25° C. | PEG-23 GDO | $R_1, R_2 = H_3C(CH_2)_7\text{-CH=CH-}(CH_2)_7$  n = 23 |
| PEG-45 Glyceryl Dioleate | 36.3° C. | PEG-45 GDO | $R_1, R_2 = H_3C(CH_2)_7\text{-CH=CH-}(CH_2)_7$  n = 45 |
| PEG-12 Glyceryl Dimyristate | Fluid @ 25° C. | PEG-12 GDM | $R_1, R_2 = CH_3(CH_2)_{12}$  n = 12 |
| PEG-23 Glyceryl Dimyristate | Fluid @ 25° C. | PEG-23 GDM | $R_1, R_2 = CH_3(CH_2)_{12}$  n = 23 |
| PEG-45 Glyceryl Dimyristate | 33.2° C. | PEG-45 GDM | $R_1, R_2 = CH_3(CH_2)_{12}$  n = 45 |
| PEG-23 Glyceryl Dipalmitate | 31.2° C. | PEG-23 GDM | $R_1, R_2 = CH_3(CH_2)_{14}$  n = 23 |
| PEG-45 Glyceryl Dipalmitate | 41.8° C. | | $R_1, R_2 = CH_3(CH_2)_{14}$  n = 45 |
| PEG-12 Glyceryl Distearate | 40.0° C. | PEG-12 GDS | $R_1, R_2 = CH_3(CH_2)_{16}$  n = 12 |
| PEG-23 Glyceryl Distearate | 39.8° C. | PEG-23 GDS | $R_1, R_2 = CH_3(CH_2)_{16}$  n = 23 |
| PEG-45 Glyceryl Distearate | 40.8° C. | PEG-45 GDS | $R_1, R_2 = CH_3(CH_2)_{16}$  n = 45 |

The derivatives listed in Table 2 were selected to sample from a broad range of specific possible structural configurations described by the generic formula seen in FIG. 3. For example, length of the PEG groups in the tested derivatives ranged from 12 to 45 units in length, and the length of the $R_1$ and $R_2$ chains ranged from 10 to 17 carbons in length. Furthermore, some of the derivatives tested included a cis-double bond between the $8^{th}$ and $9^{th}$ carbons. All of the derivatives tested showed substantial phospholipase A2 and cyclooxygenase-2 inhibitory activity. These results strongly indicate that other derivatives not tested that are similar to the structural configurations, including but not limited to those derivatives intermediate in size between the tested lipid derivatives and those somewhat outside the range of tested structural configurations, also have a very high likelihood of exhibiting substantial phospholipase $A_2$ and cyclooxygenase-2 inhibitory activity.

It is generally accepted that phospholipase $A_2$ cleaves at the C-2 of phosphate head groups of certain phospholipids, resulting in the release of free arachidonic acid. Arachidonic acid can then be converted into a variety of biologically important molecules, such as prostaglandins and thromboxins (via the cyclooxygenase pathway) and the leukotrienes (via the lipoxygenase pathway). The anti-inflammatory and antioxidizing benefits of the group of related lipid molecules of the invention are currently believed to result from the capacity of the group of related lipid molecules of the invention to inhibit the production of free arachidonic acid, by binding to the phospholipase $A_2$. It is possible that the lipids of the invention may occupy some portion of the active site of the phospholipase $A_2$, or that the lipids of the invention may bind to phospholipase $A_2$ causing a change in the shape of the phospholipase $A_2$, such that the activity of the phospholipase $A_2$ is reduced. As previously mentioned, tests have shown the lipids of the invention also inhibit the activity of Cyclooxygenase-2, and the mechanism may be the same or different from those proposed for phospholipase $A_2$. These theories are provided for convenience, and it is not intended that the applicant be bound by this explanation.

The lipids of the invention may be used in pharmaceutical compositions, foodstuffs. dietary supplements, and cosmetics. Administration of pharmaceutical compositions including one or more lipids of the group of related lipids of the invention may be accomplished using essentially any known method for pharmaceutical delivery including, for example, oral, intravenous, intramuscular, intraperitoneal, transcutaneous, intrathecal, and transmucosal. Such delivery forms typically comprise a pharmaceutically effective amount of one or more of the lipids of the group of the group of related lipids of the invention, or a mixture lipids of the group of the group of related lipids of the invention, and a pharmaceutically acceptable carrier. Specific delivery methods may include but are not limited to: capsules, caplets, lozenges, emulsions, suspensions, syrups, and powders for oral administration, sterile solutions for intravenous administration, and gels, lotions and cremes for topical application, injectables for intramuscular administration, and liquids or sprays for transmucosal administration.

Methods and means for the preparation of pharmaceutical delivery forms are generally known, and may be easily accomplished by one of ordinary skill in the art. For example Methods for administration of pharmaceuticals are discussed in DRUG DELIVERY SYSTEMS, 2nd Ed., Norris (ed.) Marcel Dekker Inc. (1989), and REMINGTON'S PHARMACEUTICAL SCIENCES, the full disclosures of which are incorporated herein by reference. Pharmaceutically acceptable carriers will include water, saline, buffers, and other compounds described, e.g., in the MERCK INDEX, Merck & Co., Rahway, N.J. See, also, BIOREVERSIBLE CARRIERS IN DRUG DESIGN, THEORY AND APPLICATION, Roche (ed.), Pergamon Press, (1987).

In still other embodiments, the lipids of the invention may be formulated in liposomes using any of the liposome manufacturing technologies known to those of skill in the art.

Therapeutic and prophylactic methods of this invention comprise the step of treating patients in a pharmaceutically acceptable manner with the compositions and mixtures described herein. The pharmaceutical compositions of the invention may be employed in a conventional manner for the treatment and prevention of certain inflammations. Such methods and prophylaxis and their dosage requirements are well recognized in the art and may be chosen by those of ordinary skill in the arts from available methods and techniques. Specific dosages and treatment regimes selected by such individual of ordinary skill will depend upon factors such as the patient's health status, the severity and course of the patient's disease, the delivery method, the treating physician's judgment, and other known factors.

Foodstuff and dietary supplement compositions including the lipids of the invention may be administered to a human or animal either alone or with other foods or beverages, as in a meal or snack. In foodstuffs, the lipids of the invention maybe used with any biologically acceptable carrier to provide safe and effective delivery of the lipids of the invention. Virtually any foodstuff or dietary supplement may be fortified with the lipids of the invention. Foodstuffs or dietary supplements containing lipids of the invention, and mixtures thereof, maybe combined with any other foodstuffs. For example, oils containing the lipids of the invention may be used as cooking oil, frying oil, salad oil, or as a component of any oil based food including but not limited to margarine, mayonnaise or peanut butter. One of ordinary skill in the art may easily formulate such foodstuffs.

The group of related lipids of the invention may also be used in mixtures and combinations with other therapeutic agents or treatments including other pharmaceutical compounds. Such combination of therapies may increase the efficacy of the group of related lipids of the invention, and/or allow a reduction in the dosage levels used of either the group of related lipids of the invention or the other therapeutic agents, thus possibly reducing possible toxicity or side effects incurred when the agents are used alone in higher dosages as monotherapies. For example, salicylic acid is an effective analgesic, but salicylic acid may cause skin inflammation if applied topically. Use of the lipids of the invention in conjunction with salicylic acid may provide several benefits. The lipids of the invention will reduce inflammation caused by the salicylic acid, and the lipids of the invention also reduce pain and discomfort independently of the salicylic acid, which may produce superior pain reduction while also reducing inflammation. Alternatively, use of the lipids of the invention may allow a reduction it the amount of salicylic acid used, without reducing the efficacy of the example composition.

Methods of the invention generally comprise the administration of the lipids of the invention in known treatment methods including administration by known pharmaceutical and dietary supplement treatment regimes. The novel group of related lipid molecules and their methods of use may be further understood by reference to the following examples.

EXAMPLE 1

The following experiment was performed in order to confirm the inhibition of phospholipase $A_2$ activity by the presence of a number of lipid molecules selected from the group of related lipids of the invention.

The activity of phospholipase $A_2$ from porcine pancreas (EC 3.1.1.4, Sigma P-6534) was measured with a chromogenic substrate, 4-nitro-3 (octanoloxy) benzoic acid as described in Methods in Enzymology, Vol. 197, pp 75–79 (1991) by Cho, W. and Kezdy, F. J. Kinetics were measured as initial rates as described by these authors with absorbance measurement at 425 nm. However, the final volume was maintained at 3.0 ml by adjusting the amount of buffer.

Inhibiting compounds were dissolved at 100 mg/ml (w/v) in the assay buffer (10 mM Tris-Hcl, pH 8.00, containing mM $CaCl_2$ and 0.1M NaCl) and maintained at 42° C. The inhibitor compound was added to the buffer in a cuvette, enzyme was added (50 μL of a 1.0 mg.ml in buffer) and maintained at 42° C. for 2 minutes. The reaction was initiated by adding substrate (50 μL in dry, chromatographic grade acetonitrile). Final inhibitor concentrations were 0.1, 1.0 and 10.0 mg/ml. The reaction rate was followed for 3 minutes. Each series of inhibitor concentrations was accompanied by a "0" inhibitor control. After addition of substrate, the reactions were stirred during the interval from 30 seconds to 90 seconds and data collection of initial rates began after 90 seconds. The absorbance of the reactions was recorded for 3 minutes and initial rates derived. The "0" inhibitor control was used for calculating the remaining activity of each sample.

More specifically, the reagents were as follows:
(a) Assay Buffer: 10 mM Tris-HCl, pH 8.00, containing 10 mM $CaCl_2$ and 0.1M NaCl
(b) Enzyme: phospholipase $A_2$, porcine pancreas EC 3.1.1.4 (Sigma P-6534), 1.0 unit hydrolyzes $1.0_{\mu mole}$ substrate per minute at 37° C., pH 8.0, phospholipase $A_2$ to 1.0 mg/ml with assay buffer and use 50 μL/reaction
(c) Substrate: 4-nitro-3-(octanoloxy) benzoic acid (Sigma Cat. #N4646), $^E$mM 4.990, 0.96 mg/ml dissolved in chromatographic grade acetonitrile and use 50 μL/reaction.

Figure 4:
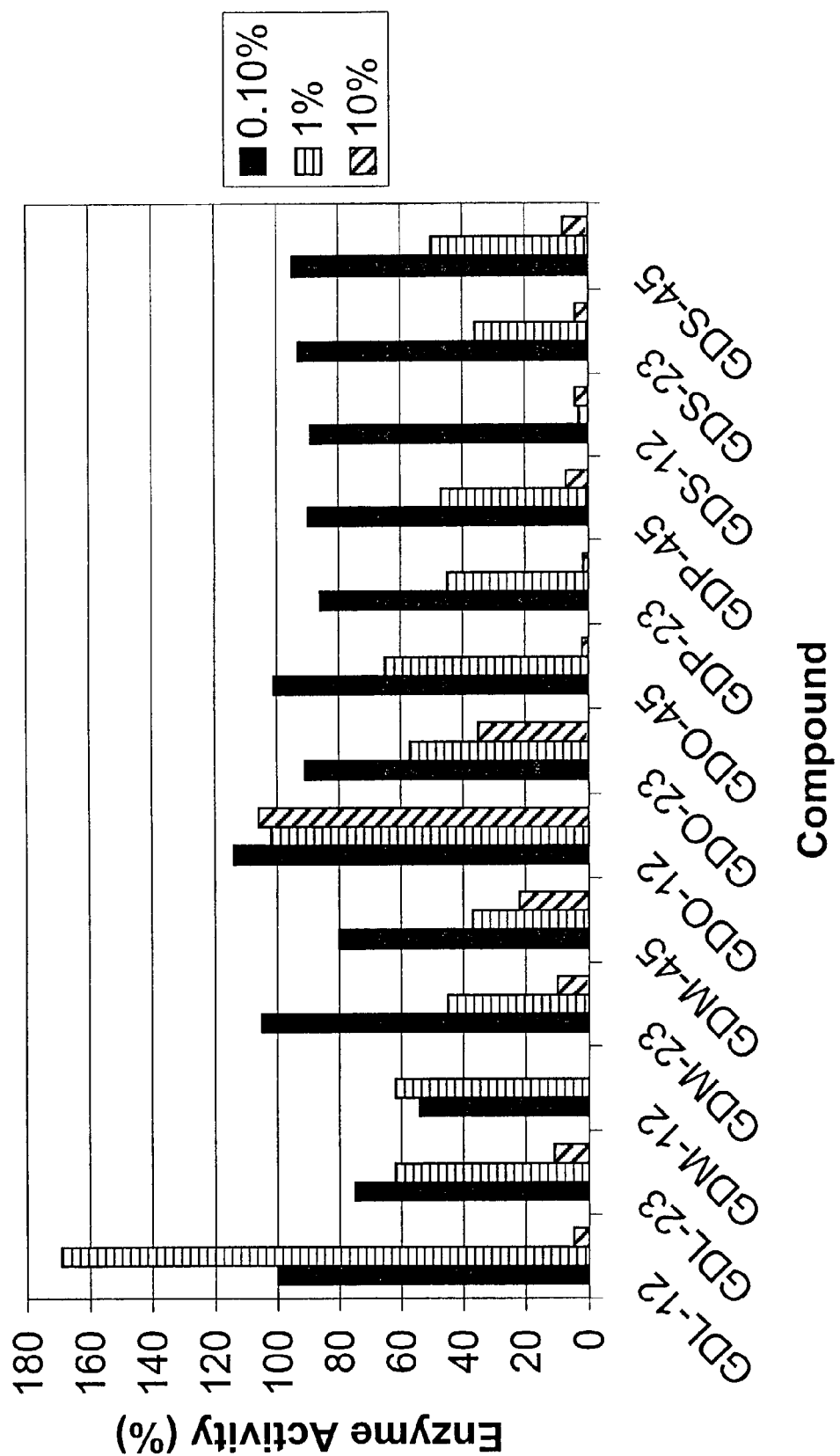
FIG. 4 is a graph showing the results of an experiment confirming significant inhibition phospholipase $A_2$ activity by selected lipid molecules of the group of related lipid molecules of the invention.

Three milliliters of the assay buffer was equilibrated at 42° C. in a water bath in quartz cuvettes. The inhibitor was added and the cuvettes were wiped and transferred to a Varian Cary 3 spectrophotometer with a peltier heater at 42° C. The enzyme was added and the mixture was equilibrated for 2 min at 42° C. The substrate was added and the contents mixed and the absorbance recorded at 425 nm after 90 seconds. As seen in FIG. 4, the results generally showed significant inhibition of phospholipase $A_2$ by the lipids of the group of related lipids that were tested.

EXAMPLE 2

The following experiment was performed in order to confirm the inhibition of activity of cyclooxygenase-2 by the presence of lipids selected from the group of related lipids of the invention.

Oxygen measurement was made with Clark electrode, with a YSI polarizer/amplifier and Linear 1200 chart recorder. The assays were performed as descried in the protocols for enzyme evaluation given by the enzyme supplier, Cayman Chemical.

A solution was created comprising the following in 1.4 ml of final reaction volume:
(1) 0.1M Tris-HCl pH 8.0
(2) 100 mM arachidonate
(3) 5 mM EDTA
(4) 2 mM phenol
(5) 1 mM heme in dimethyl sulfoxide (hemin)

The reaction was carried out as follows: Buffer, hemin, and enzyme cyclooxygenase-2 was added to the reaction chamber (calibration of the electrode was with air-saturated MilliQ purified water equilibrated at 37° C.). The inhibitor (samples of selected lipids of from the group of related lipids) was added to give final concentrations of 0.1, 1.0, or 10.0 mg/mL of the selected lipid during the reaction (successive reactions were done from lower to highest inhibitor concentrations). The chamber was closed, and inhibition of the enzyme proceeded at 37° C. for 5 min and enzyme-substrate reaction was begun by the addition of arachidonate. Rates were recorded with a Linear 1200 strip chart recorder. Input from the electrode amplifier was 50 mV per 100 chart divisions. Sensitivity was enhanced by using 10 mV full scale and offsetting the '0' of the chart 50 fold; thus providing a 5-fold increase in sensitivity. As calibrated the oxygen content was 217 nmole/mL, (340 nmole total in the 1.4 mL reaction). With 5 times scale expansion the oxygen concentration was equivalent to 0.434 nmoles of oxygen/mL/char division (100 divisions full scale). [Methods of Enzymology, Vol Vi, p. 276]

The samples were prepared as set forth in the Table 3 below:

| ITEM | CONTROL | 0.1 MG/ML OR 1.0 | 10 MG/ML |
|---|---|---|---|
| Buffer | 1.37 mL | 1/36 mL | 1.23 mL |
| Hemin | 0.014 mL | 0.014 mL | 0.014 mL |
| Enzyme | 0.002 or 0.003[1] mL | 0.002 or 0.003[1] mL | 0.002 or 0.003[1] mL |
| Inhibitor | 0.000 mL | 0.014 mL | 0.140 mL |
| Incubate capped for 5 min stirring at 37° C. | | | |
| Substrate (arachidonate) | 0.014 mL | 0.14 mL | 0.14 mL |

Figure 5:
FIG. 5 is a graph showing the results of an experiment confirming significant inhibition of cyclooxygenase-2 activity by selected lipid molecules of the group of related lipid molecules of the invention.

As seen in FIG. 5, the results generally showed significant inhibition of cyclooxygenase-2 by the selected lipids of the group of related lipids of the invention that were tested.

EXAMPLE 3

The following experiment was performed in order to evaluate the analgesic benefit of applying a topical cream containing one selected lipid from the group of related lipids of the invention.

In a double blind, patient randomized, placebo controlled crossover trial, 30 subjects with symptoms of pain and stiffness were evaluated. Each patient signed a consent form and completed a medical history form detailing a history of joint pain prior to being enrolled into this study. The objective of this study was to evaluate analgesic benefit of applying a topical cream containing PEG-12 Glyceral Distearate (see Table 2), (hereafter "PEG-12 GDS"), to body joints, on hands, feet, knees and shoulders and muscles of the neck, arms, legs and back that are affected by stiffness, soreness and pain. Subjects were assessed for pain using a visual analog scale (VAS) to record their level of pain and stiffness and a hydraulic hand dynamometer to assess changes in grip strength.

All subjects were required to mark two visual analogue scales (VAS) to record their level of pain and stiffness. Each subject was then required to use a handgrip dynamameter three times with each hand, holding the dynamometer at arms length by his or her side and alternating hands between each grip test. Each individual grip-strength, and the average of the three handgrips per hand, was recorded. After initial assessments by the blinded investigator a measured amount of either the compound containing PEG-12 GDS or the placebo was applied, by the investigator, to the areas affected by pain or stiffness. Fifteen subjects received the placebo compound and 15 subjects received the compound containing PEG-12 GDS. All assessments were then repeated at times of 5 minutes, 30 minutes, 60 minutes and 120 minutes.

The ingredients of each compound are as follows:

TABLE 4

| PEG-12 GDS Compound | PLACEBO |
|---|---|
| Purified water | Purified water |
| PEG-12 GDS | |
| Polysorbate 80 | Polysorbate 80 |
| Caprylic/Capric Triglyceride | Caprylic/Capric Triglyceride |
| Stearyl Alcohol | Stearyl Alcohol |
| Sorbitan Oleate | Sorbitan Oleate |
| Polyarylamide & C13–14 Isoparaffin & Laureth-7 | |
| Phenoxyethanol | Phenoxyethanol |
| | Carbomer |
| Hydrogenated Lecithin | |
| Imidazolidinylurea | Imidazolidinylurea |
| Methylparaben | Methylparaben |
| | Triethanolamine |
| Butylparaben | Butylparaben |
| Butylated Hydroxytoluene | Butylated Hydroxytoluene |
| Ethylparaben | Ethylparaben |
| Propylparaben | Propylparaben |

After a 5-day washout period, the subjects were crossed-over, 15 subjects received Compound A which included PEG-12 GDS and 15 subjects received a similar compound that did not contain PEG-12 GDS (hereafter the "placebo"), and each subject was re-evaluated using the same criteria.

After just one application of 2 grams of cream containing PEG-12 GDS or placebo, those individuals receiving the cream containing PEG-12 GDS experienced significantly reduced pain and stiffness. On the average, the cream containing PEG-12 GDS reduced pain by 45% compared to 15% by placebo after one dose over the first 60 minutes. In the group receiving PEG-12 GDS, pain and stiffness was reduced over the next 60 minutes while both symptoms returned in the placebo group over the same period of time. Strength also improved in the PEG-12 GDS group with an average increase of grip strength of 10% in both right and left hands compared to no improvement in strength with the placebo.

The cream containing PEG-12 GDS showed an immediate effect, within 5 minutes, of reducing pain and stiffness by as much as 72% compared to 15% for the placebo in one subject. Similarly, hand grip strength improved in the first 5 minutes, and in two subjects by as much as 50% overall, with no change for the better in the same two subjects with the placebo cream.

Figure 6:
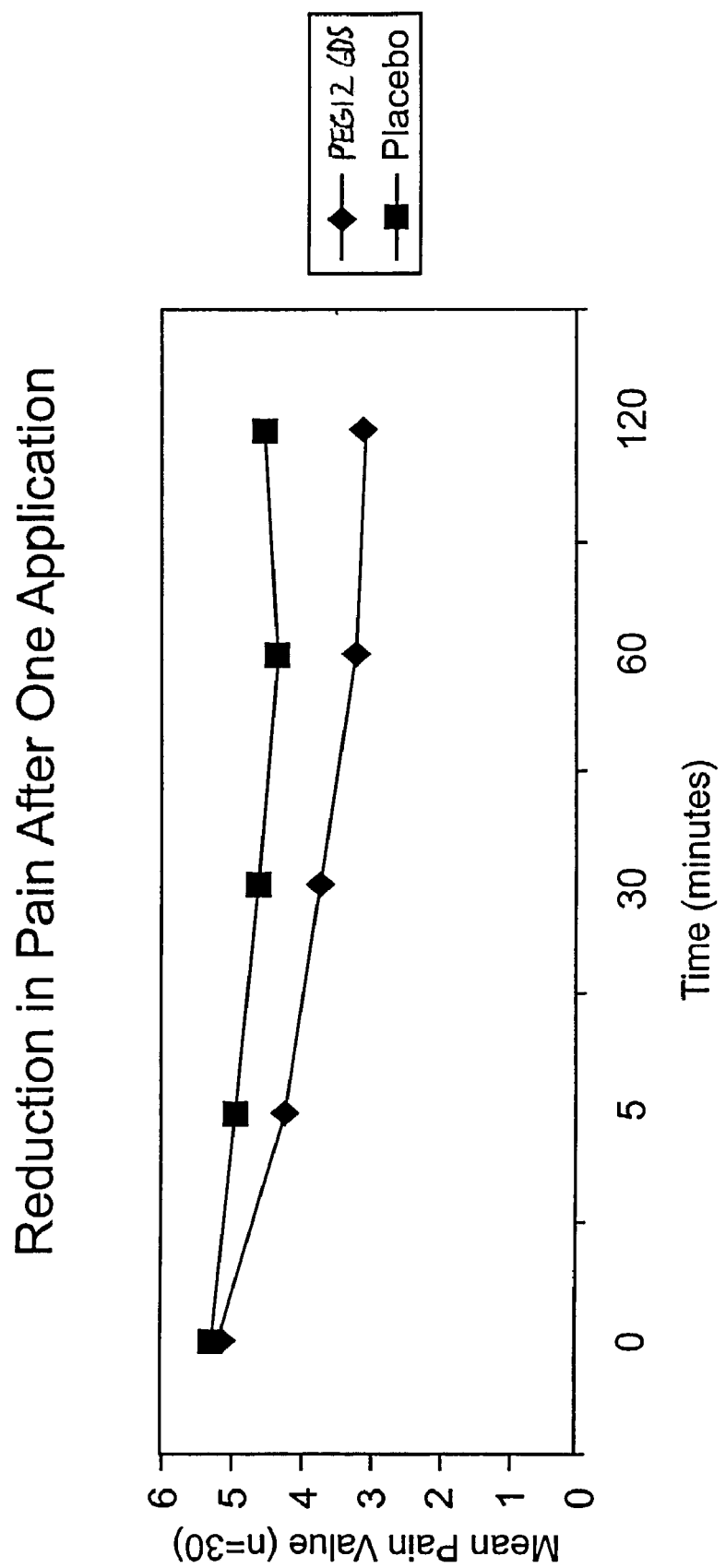
FIG. 6 is a graph showing the reduction in pain experienced by a group of individuals receiving a topical compound containing a measured amount of one selected lipid molecule from the group of related lipid molecules of the invention relative to the reduction in pain experience by a similar group receiving a placebo.

The results may be seen in FIG. 6, which shows that the PEG-12 GDS topical cream reduced pain and stiffness very quickly in subjects with mild to moderate pain after one dose. The relief of pain began within the first five minutes and lasted for the duration of the study. As expected in a placebo group, some background relief of pain and stiffness was noted within the first 60 minutes however both symptoms then began to return. This compound is also very effective in increasing handgrip strength, in both hands equally, whereas the improvement was not demonstrated when the same quantity of placebo cream was administered.

EXAMPLE 4

The following study was performed on a set of individuals. In general, each patient completed a medical history form detailing a history of joint pain prior to being enrolled into this study, and were assessed for pain using a visual analog scale (VAS) to record their level of pain and stiffness and a hydraulic hand dynamometer to assess changes in grip strength.

(a) Individual 1

A 62-year-old male suffering from both rheumatoid arthritis and osteoarthritis in his hands for 15 years. Initial pain and stiffness scores were assessed as pain 6.75, and stiffness 8.25. The patient was then instructed to apply a topical cream containing PEG-12 GDL to his hands 4 times daily for 5 days. At the end of 5 days, the patient was assessed again for pain and stiffness with scores as follows: pain 3.5 and stiffness 1.5. Furthermore, it was noted that the patient experienced a reduction in the swelling of his hands by almost 70% and was able to reduce application frequency from four times daily to twice daily.

(b) Individual 2

A 78 year old female, suffering from rheumatoid arthritis in her hands and knees for 30 years. Initial pain and stiffness scores were assessed as pain 7.5, and stiffness 7.5. The patient was then instructed to apply a topical cream containing PEG-12 GDL to her hands and knees 4 times daily for 10 days. At the end of the 10 days, the patient was assessed again for pain and stiffness with scores as follows: pain 3.5 and stiffness 3.5. Furthermore, it was noted that the patient experienced improved range of motion in both knees and hands and was able to climb stairs comfortably, whereas prior to treatment she was unable to do so without significant pain.

(c) Individual 3

A 70 year old male with a history of rheumatoid arthritis and osteoarthritis in his hands for 20 years. Initial pain and stiffness scores were assessed as pain 4, and stiffness 5. The patient was then instructed to apply a topical cream containing PEG-12 GDL to his hands 3 to 4 times daily for 6 days. At the end of the 6 days, the patient was assessed again for pain and stiffness with scores as follows: pain 2.5 and stiffness 3.5.

(c) Individual 4

A 29 year-old male who suffering from both osteoarthritis and rheumatoid arthritis in both his hands and knees. Initial pain and stiffness scores were assessed as pain 3, and stiffness 4. The patient was then instructed to apply a topical cream containing PEG-12 GDL to his hands and knees 4 times daily for 5 days. At the end of the 5 days, the patient was assessed again for pain and stiffness with scores as follows: pain 1.0 and stiffness 2.0.

EXAMPLE 5

The following experiment was performed in order to evaluate useability of the group of related lipids of the invention for decreasing skin irritation when used as a cosmetic ingredient. The study was performed on a set of individuals. Referring to Table 4, two formulas, comprising the ingredients set forth below, and containing retinyl palmitate, a Vitamin A derivative and a known skin irritant, were tested for irritancy on four human subjects. The ingredients and approximate amounts of the ingredients used are listed below.

TABLE 5

| Formula 1 | | | Formula 2 | | |
|---|---|---|---|---|---|
| Purified water | up to | 79.00% | Purified water | up to | 84.00% |
| Isopropyl myristate | | 1.50% | Isopropyl myristate | | 1.50% |
| Caprylic/Capric Triglycerides | | 1.50% | Caprylic/Capric Triglycerides | | 1.50% |
| Dimethicone | | 1.00% | Dimethicone | | 1.00% |
| Cyclomethicone | | 2.00% | Cyclomethicone | | 2.00% |
| Tocopheryl Acetate | | 0.25% | Tocopheryl Acetate | | 0.25% |
| Stearly Alcohol | | 5.00% | Stearly Alcohol | | 5.00% |
| PEG-23 Glyceryl Dipalmitate | | 5.00% | PEG-23 Glyceryl Dipalmitate | | 0.00% |
| Cetyl alcohol | | 0.00% | Cetyl alcohol | | 2.00% |
| Cholesterol | | 0.10% | Cholesterol | | 0.10% |
| BHT | | 0.10% | BHT | | 0.10% |
| Uniphen-23 | | 1.50% | Uniphen-23 | | 1.50% |
| PEG-100 Stearate | | 2.00% | PEG-100 Stearate | | 5.00% |
| Glyceryl Stearate | | 2.00% | Glyceryl Stearate | | 2.00% |
| Retinyl Palmitate | | 1.00% | Retinyl Palmitate | | 1.00% |
| Imidurea | | 0.30% | Imidurea | | 0.30% |

A measured amount (0.5 grams) of each formula was applied to the underside of each subject's forearm, and left under a plastic occlusion for 30 minutes. Upon removal of the occlusive dressing the areas of application were examined for signs and symptoms of irritation; redness, roughness, cracking, inflammation and induration. The skin where Formula 2 was applied clearly showed more objective signs of irritation compared to the areas where Formula 1 was applied.

EXAMPLE 6

The following experiment was performed in order to evaluate useability of the group of related lipids of the invention for decreasing skin irritation when used as a cosmetic ingredient. Two formulations, seen in Table 5 containing glycolic acid 10%, a known skin irritant, were applied to the underside of the forearms of four human volunteers. A measured amount was applied to the same dermatome and an occlusive dressing was placed over the test material and left for 30 minutes. The ingredients and approximate amounts of the ingredients used are listed below.

TABLE 6

| Formula 1 | | Formula 2 | |
|---|---|---|---|
| Purified water | 90% | Purified water | 80% |
| Glycolic acid | 10% | Glycolic acid | 10% |
| PEG-12 Glyceryl Dipalmitate | 0% | PEG-12 Glyceryl Dipalmitate | 10% |

Upon removal, each area, on each subject, was examined for signs and symptoms of irritation; redness, roughness, cracking, and induration. The areas where formula 2 had been applied clearly showed fewer signs of irritation and inflammation.

EXAMPLE 7

The following experiment was performed in order to evaluate useability of the group of related lipids of the invention for decreasing skin irritation when used with analgesic agents that may cause skin irritation, such as salicylic acid. Referring to Table 6, two formulations containing salicylic acid, a common ingredient in topical cosmetic creams and lotions, were applied to the faces of seven human volunteers. A measured amount (2 grams) of each material was applied by the subjects. Formula 1 was applied to the right side of the face and Formula 2 was applied to the left side. (center line was the bridge of the nose). Each subject was examined for signs and symptoms of irritation and inflammation after one hour on both sides of the face. The ingredients and approximate amounts of the ingredients used are listed below.

TABLE 7

| Formula 1 | | Formula 2 | |
|---|---|---|---|
| Purified water | 95% | Purified water | 85% |
| Salicylic Acid | 5% | Salicylic acid | 5% |
| PEG-23 Glyceryl Dimyristate | 0% | PEG-23 Glyceryl Dimyristate | 10% |

The left side of the face in all subjects showed little, or no signs of irritation and inflammation, while the right side showed redness, inflamed areas, roughness and raised areas. After two hours the left side had no further signs of irritation while the right side maintained the existing signs and symptoms.

While a number of embodiments of the invention have been described, it is apparent that the methods and compounds of the invention described may be modified to provide other embodiments of the invention. Therefore, the scope of this invention is to be defined by the appended claims rather than by the specific embodiments, which have been presented by way of example.

What is claimed is:

1. A lipid compound represented by the formula

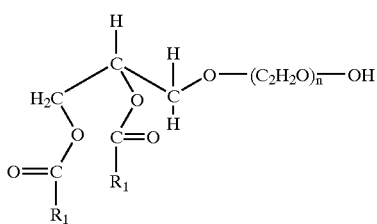

wherein $R_1$ is a long chain fatty acid, $R_2$ is a long chain fatty chain between 11 and 25 carbons in length, and wherein the variable "n" is an integer between 11 and 46, and wherein said compound is characterized by the ability to inhibit biological activity of phospholipase $A_2$.

2. The compound of claim 1, wherein said compound is further characterized by the ability to inhibit biological activity of phospholipase $A_2$ in vitro at concentrations less than or equal to 1% by volume.

3. The compound of claim 1, wherein said compound is characterized by the ability to inhibit biological activity of cyclooxygenase-2.

4. The compound of claim 1, wherein said R1 long chain fatty acid is between 11 and 25 carbons in length.

5. The compound of claim 1, wherein said R2 long chain fatty acid is between 11 and 25 carbons in length.

6. The compound of claim 1, wherein the variable "n" is an integer between 11 and 46.

7. The compound of claim 1, wherein R1 represents a long chain fatty acid selected from the group consisting of:
  (a) $CH_3(CH_2)_{10}$,
  (b) $CH_3(CH_2)_{10}(CH)_2(CH_2)_7$, and
  (c) $CH_3(CH_2)_{12}$,
  (d) $CH_3(CH_2)_{14}$,
  (e) $CH_3(CH_2)_{16}$.

8. The compound of claim 1, wherein R2 represents a long chain fatty acid selected from the group consisting of:
  (a) $CH_3(CH_2)_{10}$,
  (b) $CH_3(CH_2)_{10}(CH)_2(CH_2)_7$,
  (c) $CH_3(CH_2)_{12}$,
  (d) $CH_3(CH_2)_{14}$, and
  (e) $CH_3(CH_2)_{16}$.

9. The compound of claim 1, wherein the variable "n" is an integer between 11 and 46, and wherein R1 and R2 each represent a long chain fatty acid selected from the group consisting of:
  (a) $CH_3(CH_2)_{10}$,
  (b) $CH_3(CH_2)_{10}(CH)_2(CH_2)_7$,
  (c) $CH_3(CH_2)_{12}$,
  (d) $CH_3(CH_2)_{14}$, and
  (e) $CH_3(CH_2)_{16}$.

10. The compound of claim 1, wherein "n" is 23, and R1 and R2 are $CH_3(CH_2)_{10}$.

11. The compound of claim 1, wherein "n" is 12, and R1 and R2 are $CH_3(CH_2)_{10}(CH)_2(CH_2)_7$.

12. The compound of claim 1, wherein "n" is 23, and R1 and R2 are $CH_3(CH_2)_{10}(CH)_2(CH_2)_7$.

13. The compound of claim 1, wherein "n" is 45, and R1 and R2 are $CH_3(CH_2)_{10}(CH)_2(CH_2)_7$.

14. The compound of claim 1, wherein "n" is 12, and R1 and R2 are $CH_3(CH_2)_{12}$.

15. The compound of claim 1, wherein "n" is 23, and R1 and R2 are $CH_3(CH_2)_{12}$.

16. The compound of claim 1, wherein "n" is 45, and R1 and R2 are $CH_3(CH_2)_{12}$.

17. The compound of claim 1, wherein "n" is 23, and R1 and R2 are $CH_3(CH_2)_{14}$.

18. The compound of claim 1, wherein "n" is 45, and R1 and R2 are $CH_3(CH_2)_{14}$.

19. The compound of claim 1, wherein "n" is 12, and R1 and R2 are $CH_3(CH_2)_{16}$.

20. The compound of claim 1, wherein "n" is 23, and R1 and R2 are $CH_3(CH_2)_{16}$.

21. The compound of claim 1, wherein "n" is 45, and R1 and R2 are $CH_3(CH_2)_{16}$.

22. A composition of matter comprising one or more lipids having the formula

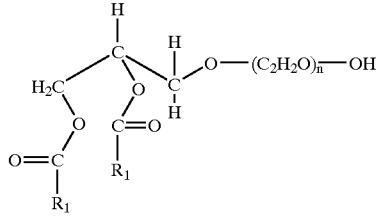

wherein $R_1$ is a long chain fatty acid chain between 11 and 25 carbons in length, $R_2$ is a long chain fatty chain between 11 and 25 carbons in length, and wherein the variable "n" is an integer between 11 and 46, and wherein said compound is further characterized by the ability to inhibit biological activity of phospholipase $A_2$.

23. The composition of matter of claim 22, wherein said compound is characterized by the ability to inhibit biological activity of phospholipase $A_2$ in vitro at concentrations less than or equal to 1% by volume.

24. The composition of matter of claim 22, wherein said compound is characterized by the ability to inhibit biological activity of cyclooxygenase-2.

25. The composition of matter of claim 22, wherein said composition is a pharmaceutical composition.

26. The composition of matter of claim 25, further comprising a pharmaceutically acceptable carrier.

27. The composition of matter of claim 22, wherein said composition is a foodstuff.

28. The composition of matter of claim 22, wherein said composition is a dietary supplement.

29. The composition of matter of claim 22, wherein said composition is a cosmetic.

30. The composition of matter of claim 26, further comprising a delivery form selected from the group consisting of: a tablet, a capsule, a syrup, a dragee, a suspension, an elixer, a solution, a powder, granules, an emulsion, microspheres, nanospheres, lipid vesicles, polymeric vesicles, or an injectable.

31. The composition of matter of claim 26, further comprising a delivery form selected from the group consisting of an ointment, a cream, a milk, an impregnated pad, a gel, a spray, and a lotion.

32. The composition of matter of claim 26, adapted for topical administration.

33. The composition of matter of claim 32, wherein said one or more lipids comprise 0.1% to 50% of the composition of matter by volume.

34. The composition of matter of claim 32, wherein said one or more lipids comprise 0.1% to 10% of the composition of matter by volume.

35. The composition of matter of claim 32, consisting essentially of:

| | |
|---|---|
| Purified water | 50.00% to 80.00% |
| Isopropyl myristate | .50% to 5.00% |
| Caprylic/Capric Triglycerides | .50% to 5.00% |
| Dimethicone | .30% to 3.00% |
| Cyclomethicone | .60% to 6.00% |
| Tocopheryl Acetate | .08% to .75% |
| Stearly Alcohol | 1.50% to 15.00% |
| PEG-23 Glyceryl Dipalmitate | 1.50% to 15.00% |
| Cholesterol | .05% to .30% |
| BHT | .05% to .30% |
| Uniphen-23 | .50% to 5.00% |
| PEG-100 Stearate | .60% to 6.00% |
| Glyceryl Stearate | .60% to 6.00% |
| Retinyl Palmitate | .30% to 3.00% |
| Imidurea | .10% to 1.00%. |

36. The composition of matter of claim 27, adapted for systemic administration.

37. The composition of matter of claim 22, wherein said compound is incorporated into a liposome.

38. The composition of matter of claim 29, further comprising a cosmetically acceptable carrier vehicle, or dilutant.

39. The composition of matter of claim 37, further a delivery form selected from the group consisting of an ointment, a cream, a milk, an impregnated pad, a gel, a spray, a lotion, a soap, and a shampoo.

40. A method for treating an inflammation related condition in a mammal comprising the step of administering a composition according to claim 28.

41. A method for treating an inflammation related condition in a mammal comprising the step of administering a composition according to claim 29.

42. A method for treating an inflammation related condition in a mammal comprising the step of administering a composition according to claim 30.

43. The method according to claim 40, wherein the inflammation related condition is selected from the group consisting of: rheumatoid arthritis, osteoarthritis, psoriasis, monoarthritis, gout, collagen vascular disease, pancreatitis, peritonitis, sepsis and shock, renal failure, atopic dermititus, and inflammatory skin conditions.

44. The method according to claim 41, wherein the inflammation related condition is selected from the group consisting of: rheumatoid arthritis, osteoarthritis, psoriasis, monoarthritis, gout, collagen vascular disease, pancreatitis, peritonitis, sepsis and shock, renal failure, atopic dermititus, and inflammatory skin conditions.

45. The method according to claim 42, wherein the inflammation related condition is selected from the group consisting of: rheumatoid arthritis, osteoarthritis, psoriasis, monoarthritis, gout, collagen vascular disease, pancreatitis, peritonitis, sepsis and shock, renal failure, atopic dermititus, and inflammatory skin conditions.

46. A method for treating an inflammation related condition in a mammal comprising the step of administering an effective amount of a composition of matter comprising one or more lipids having the formula

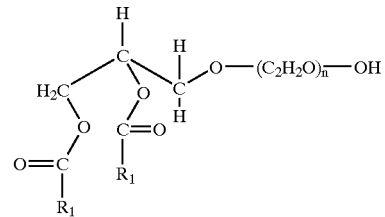

wherein $R_1$ is a long chain fatty acid between 11 and 25 carbons in length, $R_2$ is a long chain fatty between 11 and 25 carbons in length, and wherein the variable "n" is an integer between 11 and 46.

47. The method of claim 46, wherein said composition of matter is a pharmaceutical composition further comprising a pharmaceutically acceptable carrier.

48. The method of claim 46, wherein said composition of matter is a foodstuff.

49. The method of claim 46, wherein said composition of matter is a dietary supplement.

50. The method of claim 46, wherein said composition of matter is a cosmetic.

51. The method of claim 47, wherein the inflammation related condition is selected from the group consisting of: rheumatoid arthritis, osteoarthritis, psoriasis, monoarthritis, gout, collagen vascular disease, pancreatitis, peritonitis, sepsis and shock, renal failure, atopic dermititus, and inflammatory skin conditions.

52. The method of claim 48, wherein the inflammation related condition is selected from the group consisting of: rheumatoid arthritis, osteoarthritis, psoriasis, monoarthritis, gout, collagen vascular disease, pancreatitis, sepsis and shock, renal failure, atopic dermititus, and inflammatory skin conditions.

53. The method of claim 49, wherein the inflammation related condition is selected from the group consisting of: rheumatoid arthritis, osteoarthritis, psoriasis, monoarthritis, gout, collagen vascular disease, pancreatitis, peritonitis, sepsis and shock, renal failure, atopic dermititus, and inflammatory skin conditions.

54. The method of claim 47, wherein said pharmaceutical composition comprises a delivery form selected from the group consisting of: a tablet, a capsule, a syrup, a dragee, a suspension, an elixer, a solution, a powder, granules, an emulsion, microspheres, nanospheres, lipid vesicles, polymeric vesicles, an injectable, an ointment, a cream, a milk, an impregnated pad, a gel, a spray, and a lotion.

55. The method of claim 50, further comprising a delivery form selected from the group consisting of an ointment, a cream, a milk, an impregnated pad, a gel, a spray, and a lotion.

56. The composition of matter of claim 46, wherein said one or more lipids comprise 0.1% to 10% of the composition of matter by volume.

57. The method of claim 47, wherein said pharmaceutical composition is adapted for topical administration.

58. The composition of matter of claim 57, consisting essentially of:

| | |
|---|---|
| Purified water | 50.00% to 80.00% |
| Isopropyl myristate | .50% to 5.00% |
| Caprylic/Capric Triglycerides | .50% to 5.00% |
| Dimethicone | .30% to 3.00% |
| Cyclomethicone | .60% to 6.00% |
| Tocopheryl Acetate | .08% to .75% |
| Stearly Alcohol | 1.50% to 15.00% |
| PEG-23 Glyceryl Dipalmitate | 1.50% to 15.00% |
| Cholesterol | .05% to .30% |
| BHT | .05% to .30% |
| Uniphen-23 | .50% to 5.00% |
| PEG-100 Stearate | .60% to 6.00% |
| Glyceryl Stearate | .60% to 6.00% |
| Retinyl Palmitate | .30% to 3.00% |
| Imidurea | .10% to 1.00%. |

59. The composition of matter of claim 47, adapted for systemic administration.

60. The composition of matter of claim 46, wherein said compound is incorporated into a liposome.

* * * * *

UNITED STATES PATENT AND TRADEMARK OFFICE
CERTIFICATE OF CORRECTION

PATENT NO.       : 6,998,421 B2                                                          Page 1 of 2
APPLICATION NO.  : 10/229195
DATED            : February 14, 2006
INVENTOR(S)      : Brian Keller It is certified that error appears in the above-identified patent and that said Letters Patent is hereby corrected as shown below:

Figure 3:
Please substitute the following for the current Figure 3:

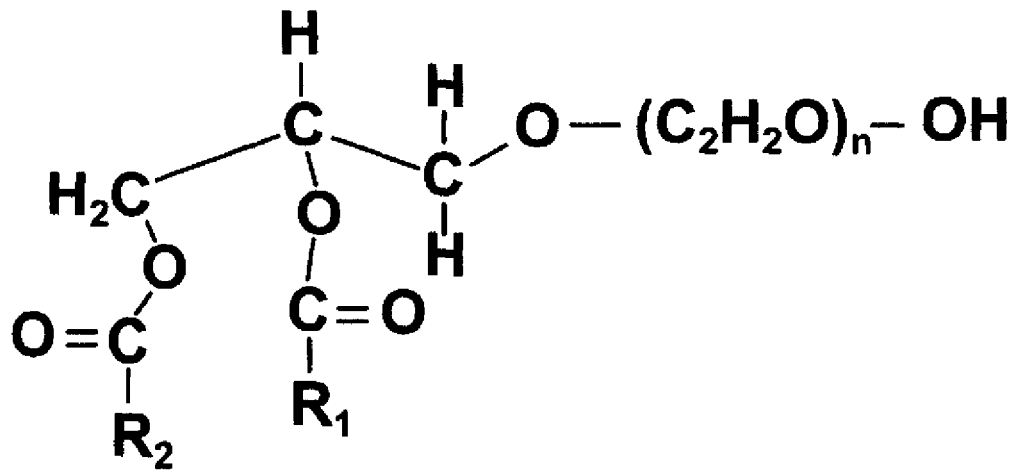

FIG. 3

Column 6, Lines 30-40:
Please replace the chemical structure shown with the following:

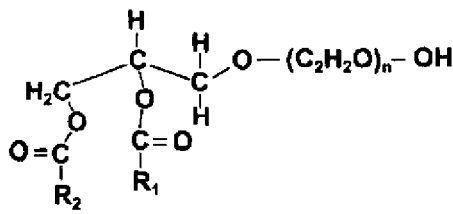

Column 6, Line 43:
Please change "preferably a long" to --preferably long--.

Signed and Sealed this
Twenty-fourth Day of April, 2012

David J. Kappos
Director of the United States Patent and Trademark Office

Column 15, Lines 40-48:
Please replace the chemical structure shown with the following:

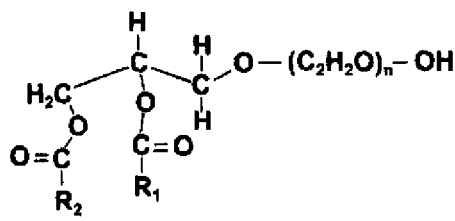

Column 15, Line 52:
Please change "fatty chain" to --fatty acid--.

Column 16, Lines 52-63:
Please replace the chemical structure shown with the following:

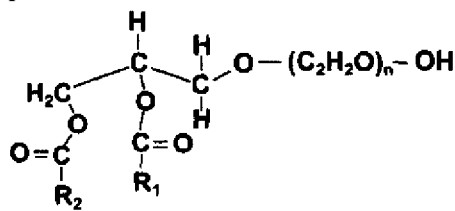

Column 16, Line 65:
Please change "long chain fatty chain" to --long chain fatty acid chain--.

Column 18, Lines 33-43:
Please replace the chemical structure shown with the following:

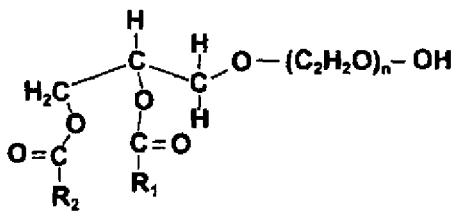

Column 18, Line 45:
Please change "long chain fatty between" to --long chain fatty acid between--.